(12) United States Patent
Birk et al.

(10) Patent No.: US 8,366,602 B2
(45) Date of Patent: Feb. 5, 2013

(54) ELECTRICALLY ACTIVATED VALVE FOR IMPLANTABLE FLUID HANDLING SYSTEM

(75) Inventors: Janel A. Birk, Oxnard, CA (US); Sean Snow, Carpinteria, CA (US)

(73) Assignee: Allergan, Inc., Irvine, CA (US)

( * ) Notice: Subject to any disclaimer, the term of this patent is extended or adjusted under 35 U.S.C. 154(b) by 627 days.

(21) Appl. No.: 12/603,058

(22) Filed: Oct. 21, 2009

(65) Prior Publication Data
US 2010/0099945 A1  Apr. 22, 2010

Related U.S. Application Data

(60) Provisional application No. 61/107,576, filed on Oct. 22, 2008.

(51) Int. Cl.
*A61F 2/00* (2006.01)
*A61F 13/00* (2006.01)
(52) U.S. Cl. .......... 600/37; 251/63.5; 251/129.06; 251/129.17; 251/129.01; 251/331
(58) Field of Classification Search .......... 600/37; 251/63.5, 129.06, 129.17, 129.01
See application file for complete search history.

(56) References Cited

U.S. PATENT DOCUMENTS

| | | | | |
|---|---|---|---|---|
| 4,340,083 | A | * | 7/1982 | Cummins ............... 137/499 |
| 4,450,375 | A | * | 5/1984 | Siegal ............... 310/331 |
| 4,671,351 | A | | 6/1987 | Rappe |
| 5,343,894 | A | * | 9/1994 | Frisch et al. ............ 137/625.65 |
| 5,669,416 | A | * | 9/1997 | Nusche ............ 137/625.44 |
| 6,024,340 | A | | 2/2000 | Lazarus et al. |
| 6,439,539 | B1 | | 8/2002 | Powell |
| 6,685,668 | B1 | | 2/2004 | Cho et al. |
| 6,715,731 | B1 | | 4/2004 | Post et al. |
| 6,729,600 | B2 | | 5/2004 | Mattes et al. |
| 6,811,136 | B2 | | 11/2004 | Eberhardt et al. |
| 6,820,651 | B2 | | 11/2004 | Seuret et al. |
| 7,040,349 | B2 | | 5/2006 | Moler et al. |
| 7,204,821 | B1 | | 4/2007 | Clare et al. |
| 2004/0000843 | A1 | * | 1/2004 | East ............... 310/331 |
| 2005/0244288 | A1 | | 11/2005 | O'Neill |
| 2005/0267406 | A1 | * | 12/2005 | Hassler, Jr. ............ 604/96.01 |
| 2006/0197412 | A1 | | 9/2006 | Rasmussen |
| 2007/0125826 | A1 | | 6/2007 | Shelton, IV |
| 2007/0156013 | A1 | | 7/2007 | Birk |

FOREIGN PATENT DOCUMENTS
WO  WO2009/132127 A1  10/2009

* cited by examiner

*Primary Examiner* — Charles A Marmor, II
*Assistant Examiner* — Sunita Reddy
(74) *Attorney, Agent, or Firm* — Linda Fox; Stephen Donovan; Debra Condino

(57) ABSTRACT

A system for facilitating obesity control includes an inflatable gastric banding device, a fluid reservoir couplable to the inflatable portion, and an implantable fluid handling device including one or more piezoelectric valves.

21 Claims, 4 Drawing Sheets

ELECTRICALLY ACTIVATED VALVE FOR IMPLANTABLE FLUID HANDLING SYSTEM

RELATED APPLICATION

This application claims priority to and the benefit of U.S. Provisional Patent Application No. 61/107,576 filed on Oct. 22, 2008, the entire disclosure of which is incorporated herein by this specific reference.

BACKGROUND

The present invention generally relates to medical devices and more specifically relates to electrically activated valves particularly for use with implantable fluid handling systems used in conjunction with gastric banding systems.

Adjustable gastric banding procedures have provided a highly effective and substantially less invasive alternative to gastric bypass surgery and other conventional surgical weight loss procedures for treating, for example, reducing or eliminating, obesity and obesity-related diseases. It has been recognized that sustained weight loss can be achieved through a laparoscopically-placed gastric band, for example, the LAP-BAND® gastric band or the LAP BAND AP® gastric band. Generally, the LAP-BAND® is placed about the cardia, or upper portion, of a patient's stomach to form a stoma that restricts the passage of food into a lower portion of the stomach. When the stoma is of an appropriate size, food held in the upper portion of the stomach provides a feeling of satiety or fullness that discourages overeating. Unlike gastric bypass procedures, laparoscopic gastric banding procedures are reversible and require no permanent modification of the gastrointestinal tract.

Over time, the stoma created by the gastric band may need adjustment in order to maintain the appropriate size which may be neither too restrictive nor too passive. Accordingly, the LAP-BAND® system provides a subcutaneous fluid access port connected to an expandable or inflatable portion of the band. By adding or removing fluid to or from the inflatable portion by means of a hypodermic needle inserted into the access port, the effective size of the band can be adjusted to provide a tighter or looser constriction.

Automatically adjustable gastric banding systems as well as remotely adjustable gastric banding systems have been proposed.

Birk, U.S. Patent Application Publication No. 2007/0156013, commonly assigned herewith and incorporated in its entirety herein by this specific reference, discloses an automatically adjustable gastric band system including an adjustment assembly that includes a sensor for sensing fluid pressure in the expandable portion of a gastric band. The adjustment assembly further includes an implantable pump connected to the expandable portion, and a controller for operating the pump to allow for automatic adjustment of the volume of the fluid in the band based on the sensed fluid pressure.

Birk et al. U.S. Patent Application Publication No. 2007/0265645 commonly assigned herewith and incorporated in its entirety herein by this specific reference, discloses a self-regulating gastric band adjustment assembly including an implantable fluid reservoir for containing a volume of the fluid useful for adjusting the band.

Coe, U.S. Pat. No. 7,338,433, commonly assigned herewith and incorporated in its entirety herein by this specific reference, discloses a remotely controllable gastric banding system including a pressurized reservoir with valves, and a controller for remotely controlling the valves from outside the patient.

There continues to remain a need for more effective, more reliable fluid handling systems and valves therefore, for use with adjustable gastric bands.

SUMMARY OF THE INVENTION

Accordingly, an improved remotely adjustable band (RAB) system for facilitating obesity control is provided by the present invention.

In one embodiment of the invention, a system for facilitating obesity control is provided wherein the system generally comprises a laparoscopically implantable gastric banding device including an inflatable chamber, and an implantable fluid handling device couplable to the fluid reservoir for controlling inflation of the inflatable chamber. The system may further include an implantable fluid reservoir couplable to the inflatable chamber and the fluid handling device. Like many proposed prior art gastric banding systems, adjustment of a stoma size in a gastric banding patient can be achieved by adjusting a volume of fluid in the inflatable chamber, for example, by controllably inflating and draining the inflatable chamber. Between adjustments to the gastric banding device, the volume of fluid contained in the inflatable portion should remain unchanged. The present invention accomplishes this by providing a fluid handling device including electrically controllable valves which have a low, or insignificant, leak rate.

More specifically, the fluid handling device generally comprises a housing having a flow path in communication with the inflatable chamber and a valve for controlling fluid passing in the fluid pathway. The valve comprises a seal element disposed along the flow path and positioned and structured to be moved between a first position, for example a sealed position in which the flow path is closed to flow, and a second position different from the first position, in which the flow path is open to flow.

The seal element may be operable by piezoelectric means. For example, in a specific embodiment, the fluid handling device further comprises a piezoelectric element sealed apart from fluid passing in the flow path. The piezoelectric element is positioned and structured to cause the seal element to be moved between the sealed position and the open position.

The system may further comprise a controller/microprocessor system includes an external or remote controller, useful for controlling the implantable fluid handling device. The controller/microprocessor may include a remote actuator effective to control movement of the seal element between the first position and the second position by controlling an electrical potential applied to the piezoelectric element.

In a specific embodiment, the seal element is biased in the sealed position, for example, by means of a spring or other suitable resilient element. The piezoelectric element is structured to bend in response to the application of an electrical potential thereto, the bending being sufficient to move the seal element away from the sealed position.

In the absence of an electrical potential across the piezoelectric element, the valve remains in a neutral position free of any significant bending stress. When flow is desired, for example, to accomplish an adjustment of stoma size, an electrical potential is applied to the piezoelectric element and the piezoelectric element bends, overcoming the bias provided by the spring. Bending of the piezoelectric element pulls the seal element off of the valve seat and flow therethrough is established.

The implantable fluid handling system is operable using no implanted ferromagnetic materials. The structure of the present invention allows moving components of the system, for example, the piezoelectric element, from contacting any of the fluid in the flow path which would increase the risk of degradation and failure of the valve.

Each and every feature described herein, and each and every combination of two or more of such features, is included within the scope of the present invention provided that the features included in such a combination are not mutually inconsistent.

BRIEF DESCRIPTION OF THE DRAWINGS

The present invention may be more clearly understood and certain aspects and advantages thereof better appreciated with reference to the following Detailed Description when considered with the accompanying Drawings of which.

DETAILED DESCRIPTION

Figure 1:
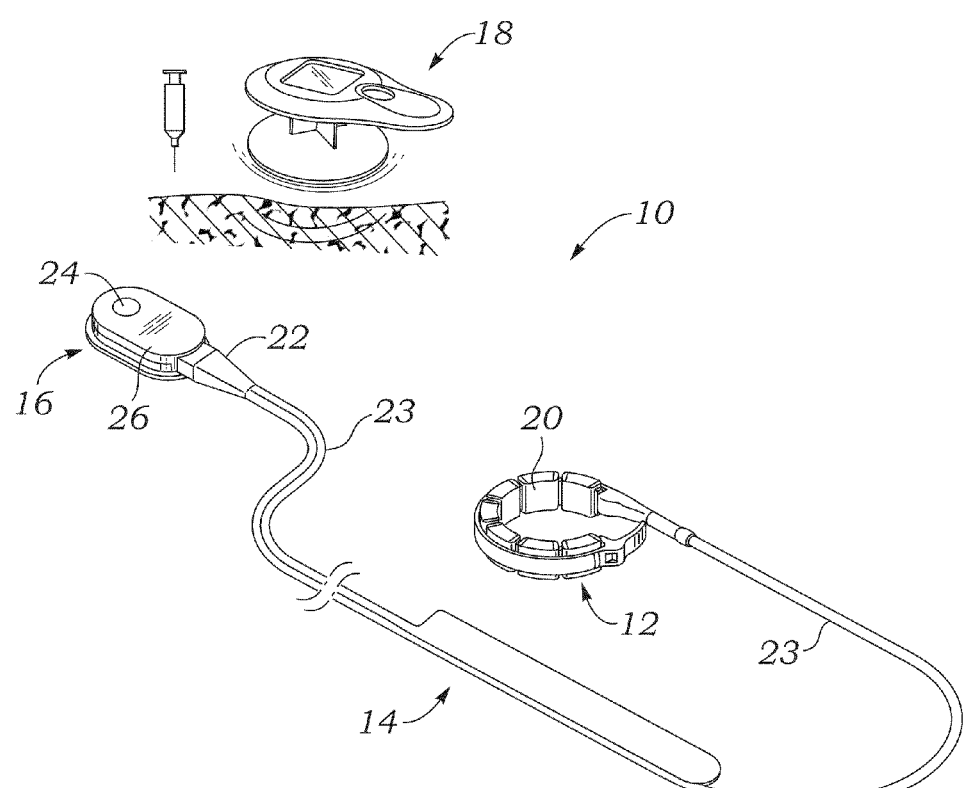
FIG. 1 is a perspective view of a gastric banding system including an implantable fluid handling system in accordance with an embodiment of the invention.
Figure 2:
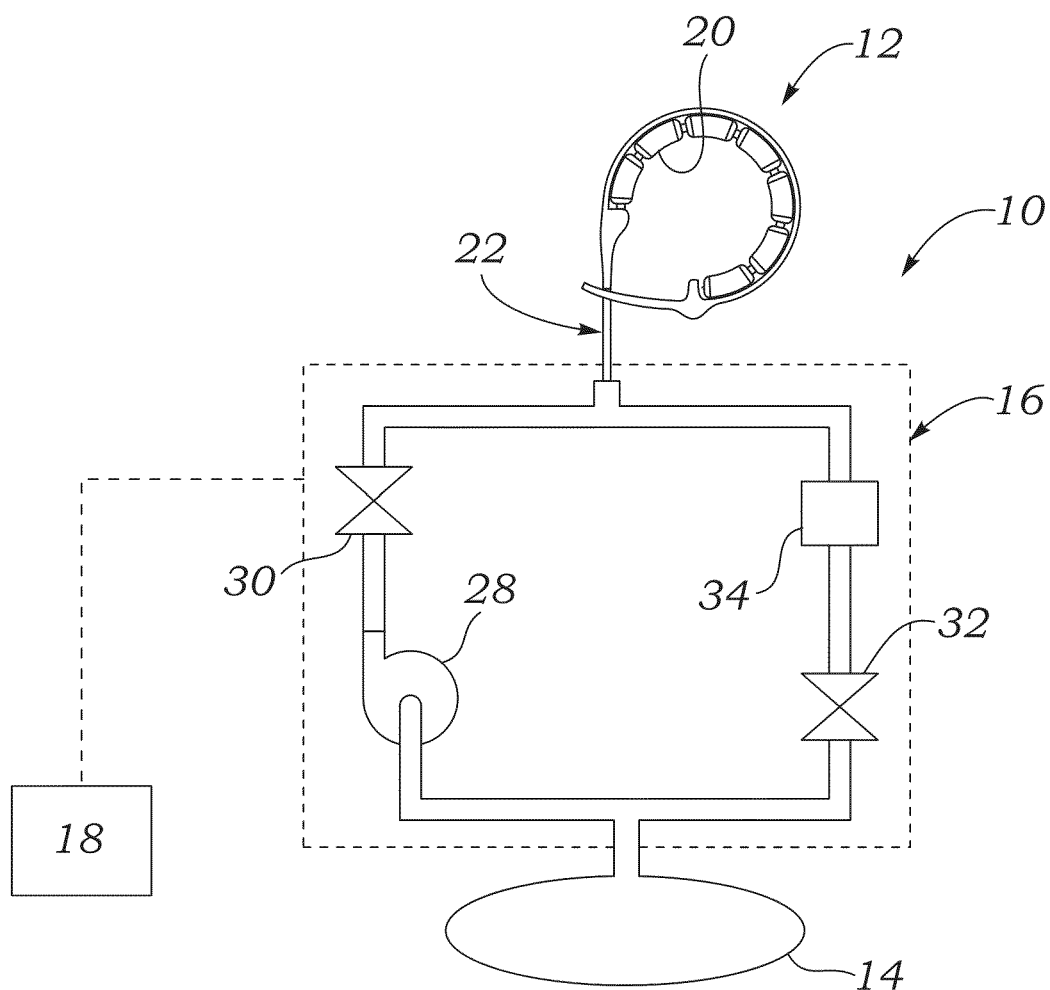
FIG. 2 is a flow diagram of the gastric banding assembly shown in FIGS. 1.

Turning now to FIGS. 1 and 2, an assembly 10 in accordance with the invention for controlling obesity or facilitating weight loss is shown. The assembly 10 generally includes a gastric band 12 having an inflatable portion 20, a fluid reservoir 14, an implantable fluid handling device 16, and a remote controller unit 18. The implantable fluid handling device 16 includes a connector 22 having inlet and outlet ports coupling the fluid reservoir 14 to the inflatable portion 20 of the gastric band 12. The remote controller unit 18 is configured to be in electronic communication, for example, radiofrequency communication, with the fluid handling system 16. The remote controller unit 18 may be further configured to be capable of receiving input from and displaying information to a human operator thereof.

It is to be appreciated that the reservoir 14, fluid handling device 16 and remote controller unit 18 may be used to replace a conventional subcutaneous fluid access port/injection port in a conventional hydraulically adjustable gastric banding system (not shown).

Surgical techniques useful for placing the present system in a gastric banding patient may be identical or similar to conventional surgical techniques used to place conventional gastric banding systems. For example, the gastric band may be placed around the stomach to form a stoma using well known laparoscopic techniques. In addition, like a conventional subcutaneous fluid access port/injection port, the present fluid handling device 16 may be sutured onto or otherwise secured to the rectus muscle sheath. The tubing from the fluid handling device 16 passes through the rectus muscle into the peritoneal cavity in the same manner as the tubing of a conventional fluid access port/injection port.

Advantageously, the system 10 of the present invention allows for a remotely controlled adjustment without needles by using the remote controller 18, or an adjustment by a needle in the override port of the fluid handling system in the event that a remote controller 18 is unavailable or if the electronics become inoperable.

In accordance with the present invention, the fluid handling device 16 is structured to move precise volumes of fluid, for example, saline, in or out of the inflatable portion 20 of the gastric band 12. The fluid handling device 16 may include an override port 24, a sealed housing 26, and internal electronic components as described elsewhere herein.

The reservoir 14 may comprise a soft, collapsible silicone balloon, for example, extending along a portion of connector tubing 28. The reservoir 14 holds a reserve of fluid used to inflate the inflatable portion 20 of the gastric band 12. By moving precisely metered or measured volumes of fluid along the tubing between the reservoir 14 and the inflatable portion 20 of the gastric band 12, a stoma size of the gastric banding patient can be precisely adjusted.

FIG. 2 illustrates a fluid flow diagram of the gastric band system 10 in accordance with one embodiment of the invention. In this embodiment, the fluid handling device 16 includes a pump 28, a first valve 30, a second valve 32 and a flow measurement device 34. The components of the fluid handling device 16 are configured to operate in a cooperative manner so as to at least facilitate regulation, adjustment and/or control of inflation of the gastric band 12. Accordingly, a most desirable stoma size of a gastric banding patient can be set, maintained and even fine tuned through operation of the pump 28 and valves 30, 32 to selectively inflate and drain the inflatable portion 20 of the gastric band 12.

The remote controller unit 18 may include a microprocessor configured to interpret command inputs from, and to provide informational data to, a human operator. In addition, the microprocessor is further configured to receive and interpret output signals, including for example pressure and/or flow rate readings, from the flow measurement device 34.

For example, the remote controller unit 18 contains electronics capable of powering and communicating with the pump 28, the first valve 30 and the second valve 32, based on operator input and/or signal output from the flow measurement device 34.

The pump 28 may comprise an electrically driven micropump, for example, an electrically driven one-way micropump, or any suitable pump useful for moving small volumes of fluid in an implanted environment.

In accordance with the present invention, at least one of valves 30, 32, for example, both of valves 30, 32, are piezoelectrically operable.

Figure 3A:
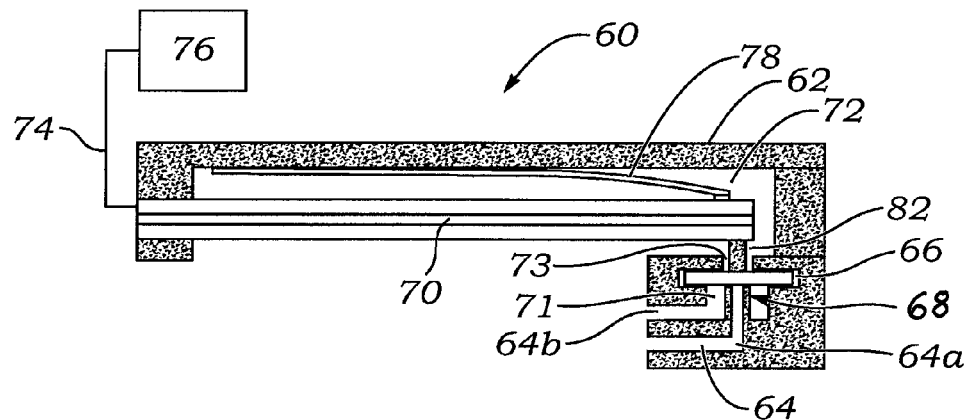
FIGS. 3A and 3B are schematic representations of a valve device of the fluid handling system of the invention shown in FIGS. 1 and 2.
Figure 3B:
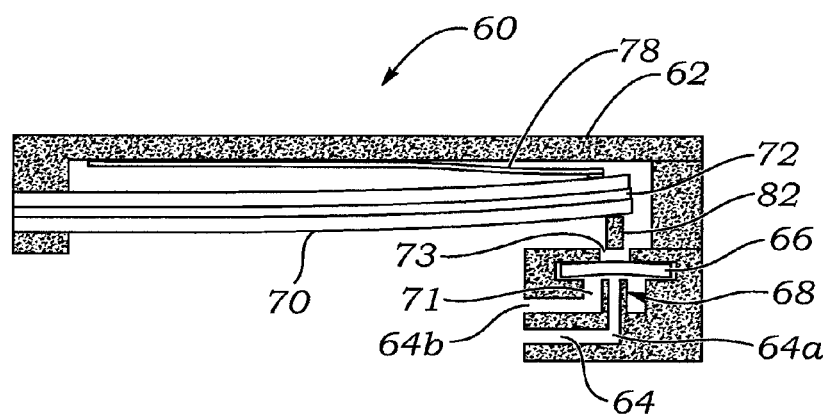

In one embodiment, valves 30, 32 are each a piezoelectric valve device 60 shown in FIGS. 3A and 3B, showing such valve 60 in an closed-to-flow (hereinafter "closed") position and an open-to-flow (hereinafter "open") position, respectively, and as described hereinafter.

Valve device 60 generally comprises a housing 62 having a flow path 64 including a first port 64a and a second port 64b, for passing of a fluid, for example, saline. A seal element 66 disposed along the flow path 64 is positioned and structured to be moved between an first position, for example, a closed position in which the seal element 66 is compressed against a valve seat 68 and closes flow between first port 64a and second port 64b (see FIG. 3A), and a second position, for example, an open position, in which the seal element 66 is spaced apart from valve seat 68 and opens flow between the first port 64a and the second port 64b (FIG. 3B). First port 64a may be in communication with reservoir 14 and second port 64b may be in communication with inflatable portion 20 of band 12, or vice-versa, using suitable fluid port connectors, not shown.

In one embodiment, the valve 60 is biased in the closed position and is only open to fluid flow when electrically activated. It is to be appreciated that, with a different arrangement of components of valve device 60, valve device 60 may be structured to be biased in an open position, said different arrangement being considered to fall within the scope of the present invention.

The valve device 60 further comprises a flexing element 70. In the embodiment shown, flexing element 70 is sealed apart, for example, substantially hermetically sealed apart, from fluid passing in the flow path 64, for example, by seal element 66. The valve 60 may be biased in the closed position and is only open to fluid flow when an electrical potential is applied to flexing element 70.

In the exemplary embodiment, housing 62 of valve device 60 may define a flow chamber 71 which includes the flow path 64, an actuator chamber 72 sealed apart from the flow chamber 71 and containing the flexing element 70, and an aperture 73.

The flexing element 70 is positioned and structured to cause the seal element 66 to be moved between the closed position or first position, and the open position or second position upon activation of the flexing element 70.

More specifically, the flexing element 70 may be piezoelectrically activatable. For example, flexing element 70 may comprise a piezoelectric material, for example, in the form of a layer, film, sheet or similar structure, which is effective to cause the flexing element 70 to bend or flex in response to the application of an electrical potential thereto. The piezoelectric material may be a piezoelectric metal, ceramic, polymer or other piezoelectrical material known to those of skill in the art.

Electrical potential can be applied to the piezoelectric element 70 by suitable means known in the art, for example, by means of a conductive lead 74 coupling piezoelectric element 70 and a voltage source 76 (not shown in FIG. 3B). Turning back briefly to FIG. 2, remote actuator 18 may be effective to control movement of the seal element 66 between the first position and the second position by controlling an electrical potential applied to the piezoelectric element.

In one embodiment, valve device 60 is structured such that in the absence of an electrical potential across flexing element 70, the flexing element 70 remains in a neutral position. A preload spring 78, for example a leaf spring or other resilient element, may be coupled to the flexing element 70 and functions to bias flexing element 70 in the neutral position. When flexing element 70 is in the neutral position, a pin 82 coupled to flexing element 70 is maintained against the seal element 66 such that the seal element 66 closes valve seat 68. As shown, pin 82 may be slidably positioned in aperture 73.

Upon application of an electrical potential to the flexing element 70, the flexing element 70 bends to a degree sufficient to overcome the bias of the preload spring 78 to allow seal element 66 to lift from valve seat 68 and thereby open flow in the flow path 64. Optionally, valve 60 may further comprise a return spring coupled to, or incorporated into, seal element 66. The return spring may be provided to facilitate lifting of the seal element 66 off the valve seat 68 (FIG. 3B).

Figure 4:
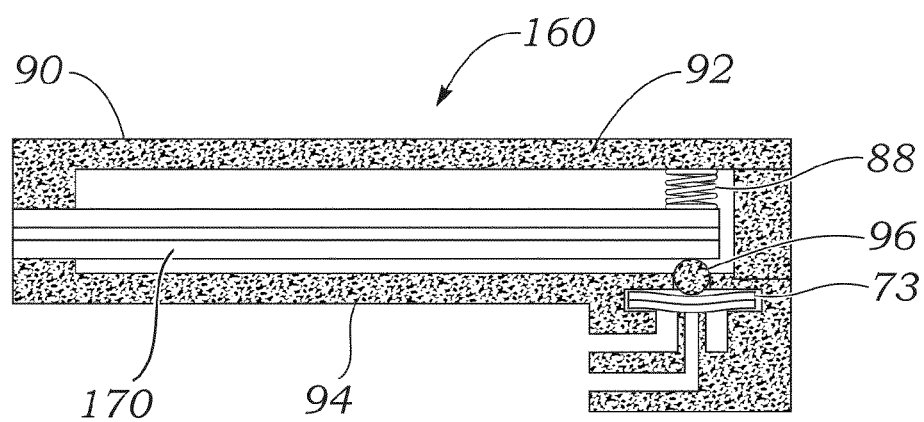
FIG. 4 is a schematic representation of an alternative valve device of the fluid handling system of the invention.

Turning now to FIG. 4, an alternative valve 160 in accordance with the invention is shown. Valve 160 is substantially identical to valve 60, with like elements represented by like numerals increased by 100.

One difference between valve 60 and valve 160 is that preload spring 78 in valve 60 has been replaced by helical spring 88 in valve 160. Further, housing 90 comprises a two layer support structure and includes an upper side 92 and a lower side 94 which may be positioned substantially parallel with flexing element 70. Further, in lieu of pin 82 of valve 60, valve 160 includes a spherical plunger element 96 seated in aperture 73.

In the exemplary embodiments shown, the valve device 60 is structured to enable rapid switch of fluid flow from no fluid flow (closed valve) to full fluid flow (open valve).

With appropriate modifications that will be known by those of skill in the art, the valve device can be modulated by changing the level of the applied voltage. If a flow sensor or pressure sensor is used in conjunction with the modulating valve, a closed loop control system can be implemented to enforce precise flow conditions.

In addition, by reversing the polarity of the electrical potential, the actuator can be made to bend in an opposing direction to enhance the valve sealing properties, for example, sealing speed. Additionally, reversing the polarity of the voltage can be used to secure the valve seal against transient high pressures.

While this invention has been described with respect to various specific examples and embodiments, it is to be understood that the invention is not limited thereto and that it can be variously practiced within the scope of the invention.

What is claimed is:

1. A system for facilitating obesity control comprising:
 a gastric banding device including an inflatable portion;
 a fluid reservoir couplable to the inflatable portion;
 an implantable fluid handling device couplable to the fluid reservoir and the inflatable portion, and including
 a valve device comprising
 a housing having a flow path for passing of a fluid,
 a seal element positioned within the housing and disposed along the flow path and positioned and structured to be moved between a closed flow position with respect to the flow path that prevents the fluid from passing through the flow path and an open flow position with respect to the flow path that allows the fluid to pass through the flow path,
 a piezoelectric element positioned within the housing and sealed apart from the flow path and positioned and structured to cause the seal element to be moved from the closed flow position to the open flow position upon application of an electrical potential to the piezoelectric element that bends the piezoelectric element away from the seal element, and
 a spring positioned within the housing and having a first end coupled to the housing and a second end coupled to the piezoelectric element such that the piezoelectric element is positioned between the seal element and the second end, the spring being biased such that the second end applies a force to the piezoelectric element that maintains the seal element in the closed flow position when no electrical potential is applied to the piezoelectric element; and
 a controller or microprocessor system in communication with the implantable fluid handling device.

2. The system of claim 1 wherein the piezoelectric element is substantially entirely sealed apart from contact with the fluid passed through the flow path.

3. The system of claim 1 wherein the piezoelectric element is structured to bend in response to the application of the electrical potential thereto, the bending being sufficient to overcome the force applied by the second end of the spring to thereby cause the seal element to be moved from the closed flow position to the open flow position.

4. The system of claim 1 wherein the piezoelectric element is structured to bend in response to the application of the electrical potential thereto, the bending being sufficient to move the seal element away from the closed flow position.

5. The system of claim 1 wherein the piezoelectric element is structured to cause the seal element to move in both a first direction to thereby open the flow path and alternately to move in a second direction to enhance sealing of the flow path upon application of an electrical potential to the piezoelectric element.

6. The system of claim 1 which is operable using no implanted ferromagnetic materials.

7. The system of claim 1 wherein the spring is a leaf spring.

8. The system of claim 1 wherein the spring is a helical spring.

9. The system of claim 1 wherein the housing includes an upper side and a lower side both positioned such that the piezoelectric element is positioned between the upper side and the lower side and the spring is positioned between the piezoelectric element and the upper side.

10. The system of claim 9 wherein the seal element is positioned within the lower side.

11. The system of claim 9 wherein the flow path is positioned within the lower side.

12. The system of claim 11 further comprising a pin coupled to the piezoelectric element and configured to apply a force from the piezoelectric element to the seal element.

13. The system of claim 12 wherein the second end is positioned above the pin.

14. The system of claim 12 wherein the second end is positioned between the pin and the upper side.

15. An implantable valve device for use in medical applications, the device comprising:
a housing having a flow path for passing of a fluid;
a seal element positioned within the housing and disposed along the flow path and positioned and structured to be moved between a closed position in which the flow path is closed to fluid flow and a second position in which the flow path is open to fluid flow;
a piezoelectric element positioned within the housing and sealed apart from the flow path and positioned and structured to cause the seal element to be moved from the closed position to the second position upon application of an electrical potential to the piezoelectric element that bends the piezoelectric element away from the seal element; and
a spring positioned within the housing and having a first end coupled to the housing and a second end coupled to the piezoelectric element such that the piezoelectric element is positioned between the seal element and the second end, the spring being biased such that the second end applies a force to the piezoelectric element that maintains the seal element in the closed position when no electrical potential is applied to the piezoelectric element.

16. The device of claim 15 further comprising a remote actuator capable of applying the electrical potential to the piezoelectric element.

17. A valve system for use in medical applications comprising:
an implantable valve device comprising
a housing including a flow path for passing of a fluid through the valve device,
a seal element disposed along the flow path and positioned and structured to be moved between a closed flow position with respect to the flow path that prevents the fluid from passing through the flow path and an open position with respect to the flow path that allows the fluid to pass through the flow path,
a piezoelectric element positioned within the housing and sealed apart from the flow path and positioned and structured to cause the seal element to be moved from the closed flow position to the open flow position upon application of an electrical potential to the piezoelectric element that bends the piezoelectric element away from the seal element, and
a spring positioned within the housing and having a first end coupled to the housing and a second end coupled to the piezoelectric element such that the piezoelectric element is positioned between the seal element and the second end, the spring being biased such that the second end applies a force to the piezoelectric element that maintains the seal element in the closed flow position when no electrical potential is applied to the piezoelectric element; and
a remote actuator effective to provide the electrical potential to the piezoelectric element.

18. The system of claim 17 wherein the remote actuator is effective to vary a level of the electrical potential provided to the piezoelectric element.

19. The system of claim 18 wherein the remote actuator is effective to modulate fluid flow in the flow path by varying a level of voltage applied to the piezoelectric element.

20. A system for facilitating obesity control comprising:
a gastric banding device comprising an inflatable chamber;
an implantable valve device comprising
a flow path in communication with the inflatable chamber;
a housing;
a seal element positioned within the housing and disposed along the flow path and positioned and structured to be moved between a closed flow position with respect to the flow path that prevents fluid from passing through the flow path and an open flow position with respect to the flow path that allows the fluid to pass through the flow path,
a piezoelectric element positioned within the housing and sealed apart from the flow path and positioned and structured to cause the seal element to be moved from the closed flow position to the open flow position upon application of an electrical potential to the piezoelectric element that bends the piezoelectric element away from the seal element, and
a spring positioned within the housing and having a first end coupled to the housing and a second end coupled to the piezoelectric element such that the piezoelectric element is positioned between the seal element and the second end, the spring being biased such that the second end applies a force to the piezoelectric element that maintains the seal element in the closed flow position when no electrical potential is applied to the piezoelectric element;
a remote actuator effective to control movement of the seal element between the closed flow position and the open flow position by controlling the electrical potential applied to the piezoelectric element.

21. The system of claim 20 wherein the remote actuator is effective to modulate fluid flow in the flow path by varying a level of voltage applied to the piezoelectric element.

* * * * *